United States Patent
Dittmann et al.

(10) Patent No.: US 7,726,307 B2
(45) Date of Patent: Jun. 1, 2010

(54) ANESTHESIA SYSTEM WITH A ANESTHETIC EVAPORATOR

(75) Inventors: Ralf Dittmann, Lübeck (DE); Jürgen Manigel, Klingberg (DE); Ralf Heesch, Lübeck (DE); Thomas Stepan, Boizenburg (DE)

(73) Assignee: Dräger Medical AG & Co. KG, Lübeck (DE)

( * ) Notice: Subject to any disclaimer, the term of this patent is extended or adjusted under 35 U.S.C. 154(b) by 463 days.

(21) Appl. No.: 11/313,062

(22) Filed: Dec. 20, 2005

(65) Prior Publication Data
US 2006/0207593 A1  Sep. 21, 2006

(30) Foreign Application Priority Data
Mar. 17, 2005  (DE) ........................ 10 2005 012 340

(51) Int. Cl.
*A61M 16/00* (2006.01)
*A61M 15/00* (2006.01)

(52) U.S. Cl. .......................... 128/203.14; 128/200.24; 128/203.12; 128/203.25

(58) Field of Classification Search ............ 128/200.24, 128/203.12, 203.13, 203.14, 203.25, 203.26, 128/204.18, 204.22, 205.11, 204.21, 204.23, 128/203.16, 203.27
See application file for complete search history.

(56) References Cited

U.S. PATENT DOCUMENTS

| 4,345,612 A | * | 8/1982 | Koni et al. | 137/101.19 |
| 4,657,710 A | * | 4/1987 | Smith et al. | 261/46 |
| 4,770,168 A | * | 9/1988 | Rusz et al. | 128/203.12 |
| 5,049,317 A | * | 9/1991 | Kiske et al. | 261/16 |
| 5,237,990 A | * | 8/1993 | Psaros et al. | 128/204.21 |
| 5,673,688 A | * | 10/1997 | Tham et al. | 128/204.22 |
| 5,832,917 A | * | 11/1998 | Sarela et al. | 128/203.12 |
| 2005/0133030 A1 | * | 6/2005 | Fiedorowicz | 128/204.13 |

FOREIGN PATENT DOCUMENTS

| DE | 41 11 138 A1 | 10/1992 |
| EP | 0 146 220 B2 | 6/1985 |

* cited by examiner

*Primary Examiner*—Justine R Yu
*Assistant Examiner*—Annette F Dixon
(74) *Attorney, Agent, or Firm*—McGlew and Tuttle, P.C.

(57) ABSTRACT

An anesthesia system with an anesthetic evaporator can be operated even in case of a defect, particularly in case of a power outage. The anesthetic evaporator (10) and a valve arranged upstream of the anesthetic evaporator (10) are provided, whereby the gas flow through the valve (8) is conveyed completely or partially through the anesthetic evaporator (10) or a bypass line (9) past the anesthetic evaporator (10) in case of operation in accordance with the regulations, while the gas flow takes place only through the anesthetic evaporator (10) in case of a defect.

20 Claims, 1 Drawing Sheet

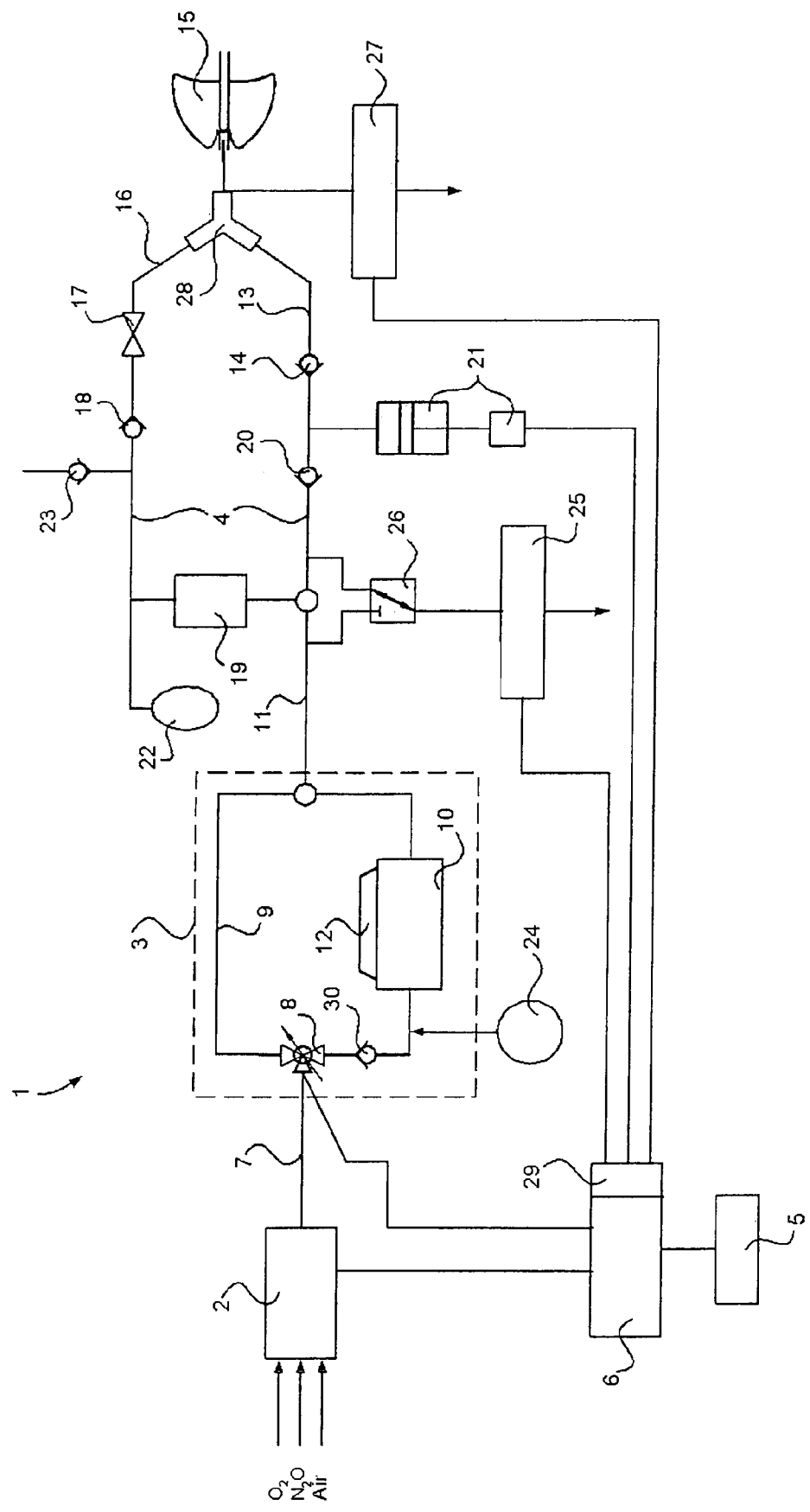

ANESTHESIA SYSTEM WITH A ANESTHETIC EVAPORATOR

CROSS REFERENCE TO RELATED APPLICATIONS

This application claims the benefit of priority under 35 U.S.C. §119 of German Patent Application DE 10 2005 012 340.6 filed Mar. 17, 2005, the entire contents of which are incorporated herein by reference.

FIELD OF THE INVENTION

The present invention pertains to an anesthesia system with an anesthetic evaporator.

BACKGROUND OF THE INVENTION

An anesthesia system with a breathing gas source, an anesthetic evaporator and a breathing system with circulation of the breathing air has become known from DE 41 11 138 A1. The breathing gas reaches the breathing system from a compressed gas source via a dispensing valve, a flow meter and the anesthetic evaporator and is fed to the patient by means of a breathing gas pump. The anesthetic evaporator operates according to the bypass principle, which is based on branching off a partial gas flow from the gas flow at the input of the anesthetic evaporator, enriching this partial gas flow in an evaporator chamber for liquid anesthetic with saturated anesthetic vapor and then adding it back to the gas flow at the output of the anesthetic evaporator. The portion of anesthetic vapor in the gas flow can be changed manually by means of an adjustment part on the anesthetic evaporator.

The prior-art anesthesia system is designed for mainly manual operation.

An anesthetic dispensing system, in which breathing gas is conveyed by means of a switching valve in fast switching sequence either through an evaporator chamber provided with saturated anesthetic vapor or via a bypass line past the evaporator chamber, has become known from EP 146 220 B2 (U.S. Pat. No. 4,657,710). The concentration of the anesthetic in the breathing gas can be changed by means of predetermining suitable control signals for the switching valve in relation to pulse width and to frequency. Sensors that detect the corresponding physical parameters are necessary for the correction of deviations in concentration that occur due to changes in temperature and pressure, so that correction factors for the concentration delivery can be calculated in a calculating and control unit.

A large number of sensors and an electric power supply are necessary for the operation of the prior-art anesthetic dispensing system.

SUMMARY OF THE INVENTION

The basic object of the present invention is to improve an electrically operated anesthesia system in such a way that it can also be operated in case of a defect and to provide a process for operating the anesthesia system.

According to the invention, an anesthesia system is provided with a breathing gas source for proving breathing gas at a gas inlet and the system having a gas outlet. An anesthetic evaporator is provided between the gas inlet and the gas outlet operating according to the bypass principle. A bypass line is provided bypassing the anesthetic evaporator. A switching means is provided at the gas inlet for completely or partially guiding breathing gas through the anesthetic evaporator or through the bypass line to the gas outlet. A control means is provided for actuating the switching means in order to change the concentration of the anesthetic at the gas outlet. A monitoring means activates the switching means in a defective state, such that the breathing gas is guided completely via the anesthetic evaporator.

According to another aspect of the invention, a process is provided for operating an anesthesia system. The process includes arranging an anesthetic evaporator operating according to the bypass principle between the gas inlet and the gas outlet, providing the switching means for the gas flow at the gas inlet and activating the switching means in such a way that the gas flow reaches the gas outlet completely or partially through the anesthetic evaporator or a bypass line bypassing the anesthetic evaporator. Further, the switching means is activated in such a way that the gas flow is conveyed completely via the anesthetic evaporator in the presence of a defective state.

Provisions are made according to the present invention to connect such an anesthetic evaporator, which operates according to the bypass principle, via a valve to a breathing gas source in such a way that the breathing gas flows completely or partially through the anesthetic evaporator or via a bypass line past the anesthetic evaporator to a gas outlet. For this purpose, the gas flow can be split by means of the valve into predetermined partial gas flows through the anesthetic evaporator and the bypass line or the valve, in the form of a switching valve, guides the gas flow alternately completely via the anesthetic evaporator or the bypass line. At the gas outlet, an anesthetic concentration is set, which lies below the value set on the anesthetic evaporator. The monitoring means is a monitoring switching circuit, which monitors the anesthesia system, is designed such that it activates the valve so that the breathing gas is guided completely via the anesthetic evaporator in the presence of a defective state, for example, a power outage.

It is advantageous that the maximum concentration delivery can only reach the set value by means of presetting a certain anesthetic concentration at the adjusting part of the anesthetic evaporator. If the gas flow is guided completely through the anesthetic evaporator, the concentration delivery can be predetermined directly at the adjusting part. If, on the other hand, the valve is actuated in a fast switching sequence as a switching valve in case of operating in accordance with the regulations, the concentration delivery may only be reduced but not increased, starting from the preset value for the anesthetic concentration. Besides a pulse-type actuation of the valve, it is particularly advantageous to design the valve as a proportional valve and to convey a certain first partial gas flow via the anesthetic evaporator and a second partial gas flow through the bypass line. The anesthetic concentration at the gas outlet results from the ratio of the partial gas flows.

A breathing gas circulation for supplying a patient with breathing gas is expediently arranged downstream of the gas outlet of the anesthetic dispensing unit. The gaseous composition of the breathing gas is monitored by two breathing gas monitors, which are attached at different points of the breathing gas circulation. A first gas monitor is designed such that it takes the gas sample either from the gas outlet of the anesthetic dispensing unit or from the inspiration line of the breathing gas circulation via a selector switch. A second breathing gas monitor is located near the patient and takes the gas sample from a Y-piece, which connects the inspiration line to the expiration line. In the monitoring of the breathing gas concentration in the breathing gas circulation, the measured values of the first gas monitor are compared with those of the second gas monitor. By switching over the first gas monitor into the gas outlet, it is possible to compare the set values of the breathing gas composition with measured values and to check for plausibility.

An oxygen source is expediently connected to the anesthetic dispensing unit as an emergency gas supply in an upwards flow manner of the anesthetic evaporator. The gas flow of the oxygen source can be adjusted manually or electrically via a control unit.

The process provided according to the present invention is to arrange an anesthetic evaporator that operates according to the bypass principle between a gas inlet and a gas outlet, to provide for a switching means for the gas flow at the gas inlet, to activate the switching means in such a way that the gas flow reaches the gas outlet through the anesthetic evaporator or a bypass line bypassing the anesthetic evaporator, and to activate the switching means, in the presence of a defective state, in such a way that the gas flow is guided completely via the anesthetic evaporator.

An exemplary embodiment of the present invention is shown in the FIGURE and is explained in detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiment of the invention is illustrated.

BRIEF DESCRIPTION OF THE DRAWING

In the drawing:

The only FIGURE is a schematic view showing an anesthesia system according to the invention.

DESCRIPTION OF THE PREFERRED EMBODIMENT

Referring to the drawings in particular, an anesthesia system 1 according to the invention comprises a digital gas mixer 2 as a breathing gas source, an anesthetic dispensing unit 3 and a breathing gas circulation 4. The gas mixer 2 is connected to compressed gas sources for oxygen, laughing gas and air, which are not shown in greater detail, and produces gas mixtures of oxygen and laughing gas or oxygen and air. Predetermined values for the gas flow and the gaseous composition are input via an input unit 5 into a control unit 6, which generates control signals for the gas mixer 2 from this. The gas mixer 2 is connected to the gas inlet 7 of a proportional valve 8 of the anesthetic dispensing unit 3.

Starting from the proportional valve 8, the breathing gas reaches a gas outlet 11 either via a bypass line 9 or an anesthetic evaporator 10 operating according to the bypass principle. A certain, not-to-be-exceeded anesthetic concentration can be adjusted at an adjusting part 12 of the anesthetic evaporator 10.

According to the values for the anesthetic concentration input via the input unit 5 at the gas outlet 11, the control unit 6 generates control signals for the proportional valve 8, by means of which the gas flow is split into a first partial gas flow through the anesthetic evaporator 10 and a second partial gas flow through the bypass line 9. Compared to the maximum value of anesthetic delivery set at the anesthetic evaporator 10, a certain percentage of the preset maximum concentration is adjusted at the gas outlet 11. A manually adjustable oxygen source 24 is connected as emergency gas supply at the input of the anesthetic evaporator 10. A nonreturn valve 30 between the feeding point of the oxygen source 24 and the proportional valve 8 eliminates a back flow of oxygen in the direction of the proportional valve 8.

In the breathing gas circulation 4, breathing gas flows via an inspiration line 13 and an inspiration valve to a patient 15 and in case of expiration via an expiration line 16, a pressure relief valve 17, for adjusting an end expiratory pressure, an expiration valve 18 and a carbon dioxide absorber 19 and a directional valve 20 back into the inspiration line 13. In case of artificial respiration, the breathing gas is fed to the patient 15 by means of an electrically operated breathing gas pump 21. A separate manual respiration pouch is provided for manual respiration. At the end of expiration, excess breathing gas is released via an excess gas release valve 23 into an anesthetic gas conduction, not shown in greater detail.

A first breathing gas monitor 25 is connected via a selector switch 26, such that it, depending on the position of the selector switch 26, either measures the gas concentration in the breathing gas circulation 4 or at the gas outlet 11 of the anesthetic dispensing unit 3. A second breathing gas monitor 27 takes a gas sample to be analyzed at a Y-piece 28 in the immediate vicinity of the patient 15.

The anesthesia system 1 according to the present invention operates as follows:

According to the predetermined values for the anesthesia input via the input unit 5, a predetermined breathing gas flow is fed via the gas outlet 11 into the breathing gas circulation 4. The breathing gas composition results from the set values of the digital gas mixer 2 and the switching position of the proportional valve 8, with which a predetermined percentage of the maximum anesthetic concentration preselected at the adjusting part 12 is added to the breathing gas. For monitoring the anesthetic concentration delivery, the selector switch 26 is adjusted such that the gas sample for the first gas monitor 25 is taken from the gas outlet 11. The maximum anesthetic concentration set at the adjusting part 12 can be determined from the control data of the proportional valve 8, which are an indicator of the gas splitting between the anesthetic evaporator 10 and the bypass line 9. In this switching position of the selector switch 26, a plausibility comparison is also carried out between the adjusting data at the digital gas mixer 2 and the measured concentrations of the individual gas components at the first gas monitor 25.

In respiration operation, the selector switch 26 is set on the switching position shown in the FIGURE, in which the breathing gas sample is taken from the breathing gas circulation 4. A plausibility comparison can now be carried out between the measured values of the first breathing gas monitor 25 and of the second gas monitor 27.

If a deviation regarding anesthetic delivery is found in the plausibility comparison, the proportional valve 8 receives corresponding control signals from a monitoring switching circuit 29 in order to completely convey the gas flow via the anesthetic evaporator 10. The user is informed by an alarm signal and may adjust the desired anesthetic concentration on the adjusting part 12. Subsequently, the selector switch 26 is actuated in such a way that the gas sampling for the first gas monitor 25 takes place from the gas outlet 11. The set value at the anesthetic evaporator 10 and the measured anesthetic concentrations at the first gas monitor 25 can then be compared to each other.

After that, the selector switch 26 is brought to the switching position shown in the FIGURE for the gas sampling from the breathing gas circulation 4. In this switching position, the measured values for the anesthetic concentration of the gas monitors 25, 27 are checked against each other for plausibility.

In case of a power outage, in which the gas mixer 2, the gas monitors 25, 27 and the control unit 6 are not operable, breathing gas is fed into the breathing gas circulation 4 from the separate oxygen source 24 via the anesthetic evaporator 10. The respiration strokes are generated by the manual respiration pouch 22. The anesthesia system 1 according to the present invention is thus ready for use even without power.

While specific embodiments of the invention have been shown and described in detail to illustrate the application of the principles of the invention, it will be understood that the invention may be embodied otherwise without departing from such principles.

What is claimed is:

1. An anesthesia system, comprising:
    an anesthetic evaporator with a gas inlet and a gas outlet, the anesthetic evaporator operating according to the bypass principle between the gas inlet and the gas outlet;
    a breathing gas source for supplying breathing gas at the gas inlet;
    a bypass line bypassing the anesthetic evaporator;
    a switching means at said gas inlet for selectively completely or partially guiding breathing gas of said breathing gas source through the anesthetic evaporator or through the bypass line to the gas outlet;
    a control means for actuating the switching means in order to change the concentration of the anesthetic at the gas outlet; and
    a monitoring means for activating the switching means in a defective state, such that breathing gas is guided completely via the anesthetic evaporator to the gas outlet.

2. An anesthesia system in accordance with claim 1, further comprising a breathing gas circulation for supplying a patient with breathing gas, said breathing gas circulation is arranged downstream of the gas outlet.

3. An anesthesia system in accordance with claim 2, further comprising: breathing gas monitors for determining the gaseous composition of the breathing gas wherein said breathing gas circulation has an inspiration line and an expiration line connected to a Y-piece for connection to a patient and said breathing gas monitors include a first gas monitor connected via a selector switch to the gas outlet and to the inspiration line for selective gas sampling from the gas outlet or from the inspiration line and a second breathing gas monitor for taking a gas sample near the patient in the area of the Y-piece.

4. An anesthesia system in accordance with claim 1, further comprising an oxygen source connected as emergency gas supply upstream of the anesthetic evaporator to provide breathing gas thereto.

5. An anesthesia system in accordance with claim 4, wherein the breathing gas is taken from the oxygen source in the presence of a defective state as the breathing gas guided completely via the anesthetic evaporator to the gas outlet.

6. An anesthesia system in accordance with claim 1, wherein the switching means comprises a proportional valve conveying predetermined partial gas flows through the anesthetic evaporator and the bypass line.

7. An anesthesia system in accordance with claim 1, wherein the switching means comprises a switching valve conveying the gas flow in a fast switching sequence either through the anesthetic evaporator or the bypass line.

8. A system in accordance with claim 1, wherein:
    said anesthetic evaporator includes an adjusting part for adjusting an anesthetic concentration generated by said anesthetic evaporator, said adjusting part of said anesthetic evaporator being set at a maximum concentration for patient.

9. A process for operating an anesthesia system, the process comprising the steps of:
    arranging an anesthetic evaporator along a line between a gas inlet and a gas outlet and with a bypass line between the gas inlet and the gas outlet for bypass operation of the anesthetic evaporator between the gas inlet and the gas outlet;
    providing a switch for switching a gas flow at the gas inlet;
    activating the switch in such a way that the gas flow selectively reaches the gas outlet completely or partially through the anesthetic evaporator or through the bypass line bypassing the anesthetic evaporator; and
    activating the switch such that gas flow is conveyed completely via the anesthetic evaporator in the presence of a defective state.

10. A process in accordance with claim 9, further comprising:
    connecting an oxygen source as an emergency gas supply for supply of gas upstream of the anesthetic evaporator;
    wherein said step of activating the switch such that gas flow is conveyed completely via the anesthetic evaporator in the presence of a defective state includes switching off of a breathing gas source in the presence of the defective state and taking the breathing gas from the oxygen source to form the gas flow in the presence of the defective state.

11. A process in accordance with claim 10, further comprising:
    operating the anesthetic evaporator at a maximum concentration for patient.

12. A process for operating an anesthesia system, the process comprising the steps of:
    providing a breathing gas source for supplying breathing gas;
    providing an anesthetic dispensing unit with an inlet and an outlet, said inlet being connected to said breathing gas source and receiving the breathing gas, said anesthetic dispensing unit including a bypass line connecting said inlet to said outlet, said anesthetic dispensing unit also including an anesthetic evaporator connected to said inlet and said outlet, said anesthetic evaporator including an adjusting part for adjusting an anesthetic concentration generated by said anesthetic evaporator, said anesthetic dispensing unit including a valve at said gas inlet for selectively guiding the breathing gas completely through said anesthetic evaporator and not through said bypass line, or said valve guiding the breathing gas partially through the anesthetic evaporator and partially through said bypass line;
    adjusting said adjusting part of said anesthetic evaporator to a maximum concentration for a patient;
    controlling said breathing gas source and said valve to deliver breathing gas with anesthetic at said outlet, with said anesthetic in the breathing gas being at a concentration lower than said maximum concentration;
    determining a defective state in the anesthesia system;
    activating said valve to guide the breathing gas completely through said anesthetic evaporator when said defective state has been determined.

13. A process in accordance with claim 12, further comprising:
    providing a manual oxygen source connected to an inlet of said anesthetic evaporator;
    during a determination of said defective state, manually operating said manual oxygen source to supply oxygen to said anesthetic evaporator.

14. A process in accordance with claim 12, further comprising:
providing a breathing gas circulation for supplying a patient with breathing gas, said breathing gas circulation being arranged downstream of said outlet of said anesthetic dispensing unit.

15. A process in accordance with claim 14, further comprising:
providing an inspiration line and an expiration line in said breathing gas circulation, said inspiration line and said expiration line being connected to a Y-piece for connection to a patient;
providing a carbon dioxide absorber between said expiration line and said inspiration line for feeding exhaled breathing gas from the expiration line back into the inspiration line downstream of said anesthetic dispensing unit;
providing a first gas monitor connected via a selector switch to selectively connect said first gas monitor to either said gas outlet of said anesthetic dispensing unit or to said inspiration line downstream of said carbon dioxide absorber;
providing a second gas monitor for measuring the breathing gas in an area of said Y-piece;
comparing results of said first and second gas monitors to determine said defective state.

16. A process in accordance with claim 15, further comprising:
providing a manual oxygen source connected to an inlet of said anesthetic evaporator;
during a determination of said defective state,
controlling said breathing gas source to stop supplying the breathing gas to said inlet of said anesthetic dispensing unit; and
manually operating said manual oxygen source to supply oxygen to said anesthetic evaporator.

17. A process in accordance with claim 16, further comprising:
a manual respiration pouch connected to said breathing gas circulation and for generating respiration strokes through said breathing gas circulation during said defective state.

18. A process in accordance with claim 15, wherein:
said manual oxygen source feeds oxygen to said inlet of said anesthetic evaporator without the oxygen passing through said valve of said anesthetic dispensing unit.

19. A process in accordance with claim 12, wherein:
said breathing gas source provides a plurality of different breathing gases to said valve of said anesthetic dispensing unit.

20. A process in accordance with claim 12, wherein:
said valve of said anesthetic dispensing unit selectively guides the same breathing gas from said breathing gas source either through said anesthetic evaporator or through said bypass line.

\* \* \* \* \*